US00PP36390P2

(12) United States Plant Patent
Hachmann

(10) Patent No.: US PP36,390 P2
(45) Date of Patent: Jan. 14, 2025

(54) ***DASIPHORA* PLANT NAMED 'Hachrosa'**

(50) Latin Name: ***Daisphora fruticosa* subsp. *fruiticosa***
Varietal Denomination: Hachrosa

(71) Applicant: Holger Hachmann, Barmstedt (DE)

(72) Inventor: Holger Hachmann, Barmstedt (DE)

(73) Assignee: H. HACHMANN INH. HOLGER HACHMANN, Barmstedt (DE)

( * ) Notice: Subject to any disclaimer, the term of this patent is extended or adjusted under 35 U.S.C. 154(b) by 0 days.

(21) Appl. No.: 18/637,530

(22) Filed: Apr. 17, 2024

Related U.S. Application Data

(60) Provisional application No. 63/460,510, filed on Apr. 19, 2023.

(51) Int. Cl.
*A01H 5/02* (2018.01)
*A01H 6/74* (2018.01)

(52) U.S. Cl.
USPC ..... Plt./237

(58) Field of Classification Search
USPC ..... Plt./226, 237
See application file for complete search history.

(56) References Cited

U.S. PATENT DOCUMENTS

PP9,874 P * 4/1997 Lenz ..... Plt./237

* cited by examiner

*Primary Examiner* — Karen M Redden
(74) *Attorney, Agent, or Firm* — Penny J. Aguirre

(57) ABSTRACT

A new cultivar of *Dasiphora* plant named 'Hachrosa' that is characterized by its compact plant habit, its matte, grey-green foliage, and its flowers that are lilac pink in color with red-pink centers and fade very little after opening.

1 Drawing Sheet

Botanical classification: *Dasiphora fruticosa* subsp. *fruiticosa.*

Variety denomination: 'Hachrosa'.

BACKGROUND OF THE INVENTION

The present invention relates to a new and distinct cultivar of *Dasiphora fruticosa* subsp. *fruiticosa* (syn. *Dasiphora fruticosa*, syn. *Potentilla fruticosa*). The new cultivar will be referred to hereafter by its cultivar name, 'Hachrosa'. 'Hachrosa' is a new cultivar of deciduous shrub grown for landscape use.

The new cultivar is the result of a controlled breeding program conducted by the Inventor in Barmstedt, Germany. The intent of the breeding program is to develop new cultivars of *Dasiphora* with compact plant habits, unique flower colors and abundant flowering. The new cultivar arose from a cross made by the Inventor in Barmstedt, Germany in summer of 2000 between the cultivars 'Rosiflor' (not patented) as the female parent and 'Red Ace' (not patented) as the male parent. The Inventor selected 'Hachrosa' as a single unique plant amongst the seedlings that resulted from the above cross in summer of 2006.

Asexual propagation of the new cultivar was first accomplished by softwood cuttings by the Inventor in Barmstedt, Germany in August of 2006. Asexual propagation by softwood cuttings has determined that the characteristics of the new cultivar are stable and reproduced true to type in successive generations.

SUMMARY OF THE INVENTION

The following traits have been repeatedly observed and represent the characteristics of the new shrub rose. These attributes in combination distinguish 'Hachrosa' as a unique cultivar of *Dasiphora.*

1. 'Hachrosa' exhibits a compact plant habit.
2. 'Hachrosa' exhibits matte, grey-green foliage.
3. 'Hachrosa' exhibits flowers that are lilac pink in color with red-pink centers and fade very little after opening.

The female parent plant of 'Hachrosa' differs from 'Hachrosa' in having flowers that are slightly smaller and deeper pink in color with centers that are darker pink in color. The male parent plant of 'Hachrosa' differs from 'Hachrosa' in having smaller flowers that are orange-red to red in color. 'Hachrosa' can also be compared to the *Dasiphora fruticosa* subsp. *fruiticosa* cultivars 'Pink Beauty' (U.S. Plant Pat. No. 9,874) and 'Hachapp'. Both are similar to 'Hachrosa' in having flowers that are pinkish in color. 'Pink Beauty' differs from 'Hachrosa' in having a less compact plant habit, flowers that are entirely pink in color that fade to a lighter pink color after opening. 'Hachapp' differs from 'Hachrosa' in having flowers that are salmon pink in color with yellow centers.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures includes a website listing by Landwirtschaftskammer Schleswig-Holstein.

BRIEF DESCRIPTION OF THE DRAWING

The accompanying color photograph illustrates the overall appearance and distinct characteristics of the new *Dasi-*

*phora*. The photograph was taken of a 1.5-year-old plant as grown outdoors in a 1.5-liter container at a nursery in Barmstedt, Germany. The photograph in provides a close-up view of a plant of 'Hachrosa' in bloom. The colors in the photographs are as close as possible with the photographic and printing technology utilized and the color values cited in the detailed botanical description accurately describe the colors of the new *Dasiphora*.

DETAILED BOTANICAL DESCRIPTION

The following is a description of 3-year-old plants as field grown in Boskoop, The Netherlands. The phenotype of the new cultivar may vary with variations in environmental, climatic, and cultural conditions, as it has not been tested under all possible environmental conditions. The color determination is in accordance with The 2019 Colour Chart of The Royal Horticultural Society, London, England, except where general color terms of ordinary dictionary significance are used.

General description:

*Blooming period*.—May into July in Germany.

*Plant type*.—Deciduous shrub.

*Plant habit*.—Broadly spreading and upright, globular.

*Height and spread*.—An average of 60 cm in height and 70 cm in width as a mature plant in the landscape.

*Hardiness*.—At least in U.S.D.A. Zones 3 to 8.

*Diseases and pests*.—Low susceptibility to powdery mildew has been observed in Germany (caused by *Podosphaera* sp. and other unknown causative agents), no susceptibility or resistance to pests has been observed).

*Propagation*.—Softwood cuttings.

*Root description*.—Fibrous.

*Growth rate*.—Low to moderate.

*Root development*.—Cuttings initiate roots in 6 to 8 weeks and a fully rooted cutting plant is produced in 10 months.

Branch description:

*Branch shape*.—Rounded.

*Branch color*.—Young; 138D, mature; 166B.

*Branch surface texture*.—Moderately pubescent; covered with short soft hairs an average of 0.5 mm in length and NN155D in color, older bark exfoliating in small strips.

*Branching*.—Freely branching.

*Branch size*.—An average of 20.2 cm in length and 1.5 mm in diameter.

*Branch quantity*.—Main; 40, lateral; 360.

*Internode length*.—Average of 5.5 mm.

Foliage description:

*Leaves*.—Compound, alternate arrangement, flat aspect, reniform in shape, an average of 1.35 cm in length, 1.8 in width, 37 leaves per branch, leaf venation is pinnate.

*Leaflets*.—5, occasionally 3, elliptic to obovate in shape, acute apex and base, entire margins, an average of 1.5 cm in length and 3 mm in width, unlobed, both surfaces matte, upper surface sparsely to moderately pubescent, lower surface moderately pubescent, hairs are soft, 0.5 mm in length, NN155D in color, color; young upper surface 143C, young lower surface 144B, mature upper surface 137A to 137B, veins N138B, mature lower surface 138B, veins 146C.

*Stipules*.—Narrow oblong in shape, both sides smooth and glabrous, matte, 7 mm in length, 2 mm in width, top cleft, base narrow cuneate, color both surfaces; N199D, veined 200C.

*Petioles*.—An average of 7.5 mm in length and 0.8 mm in diameter, medium to high strength, color; upper surface 143B, lower surface 146D, surface is moderately pubescent short hairs 0.75 mm in length, NN155D in color.

Inflorescence description:

*Inflorescence type*.—Solitary, terminal and axillary at upper nodes of stems.

*Flower number*.—An average of 10 per main stem, 700 flowers and buds per plant.

*Flower fragrance*.—None.

*Flower longevity*.—About 5 days, self-cleaning.

*Flower type*.—Single, rotate.

*Flower aspect*.—upright to outward.

*Flower size*.—An average of 2.3 cm in diameter and 6 mm in depth.

*Pedicels*.—An average of 3 mm in length, 1 mm in diameter, held in a 7.5° angle, 138C in color, surface is matte, and is densely covered with soft, short hairs, average of 0.5 mm in length, NN155D in color.

*Flower buds*.—Nearly spherical in shape, an average of 6 mm in diameter and length, 150B to 150C in color, surface is smooth, sparsely to moderately pubescent with soft, short hairs, 1.5 mm in length, NN155D in color.

*Sepals*.—5, placed in one whorl, deltoid in shape, entire margins, 5 mm in length, 3.5 mm in width, broadly cuneate base, acute apex, upper surface smooth and glabrous, lower surface moderately pubescent with short hairs, 1 mm in length, too small to measure color, color; when opening and fully open upper surface 150B, margins and tips 151A, when opening and fully open lower surface 150B to 150C.

*Petals*.—5, occasionally 6, 1 whorl, broadly obovate to nearly orbicular in shape, obtuse apex, cuneate base, margins are entire and slightly undulate, both surfaces are smooth, glabrous, and matte, color; when opening upper surface 63B, center 63C, base 53D, when opening lower surface a blend of 36C and 36D, margins 51D, tinged at the base 5D, when fully open upper surface 63C, center a blend of 63C to 63D, base 5D, when fully open lower surface a blend of 36C to 36D, margins 51D, base tinged 5D.

*Calyx*.—Rotate, 1.5 mm in length, 15 cm in diameter.

Reproductive organs:

*Pistils*.—Average of 60, 1 mm in length, stigma; club-shaped, 0.2 mm in length, diameter, N172A in color, style; 0.8 mm in length, 5C in color, ovary; 143C in color.

*Stamens*.—30 per flower, filaments; average of 2 mm in length, 5D in color, anthers; average of 1 mm in length and 0.75 mm in width, short oblong in shape, 12A in color, pollen; low in quantity, 12C in color.

*Fruit and seed*.—Have not been observed to date.

It is claimed:

1. A new and distinct cultivar of *Dasiphora* plant named 'Hachrosa' as herein illustrated and described.

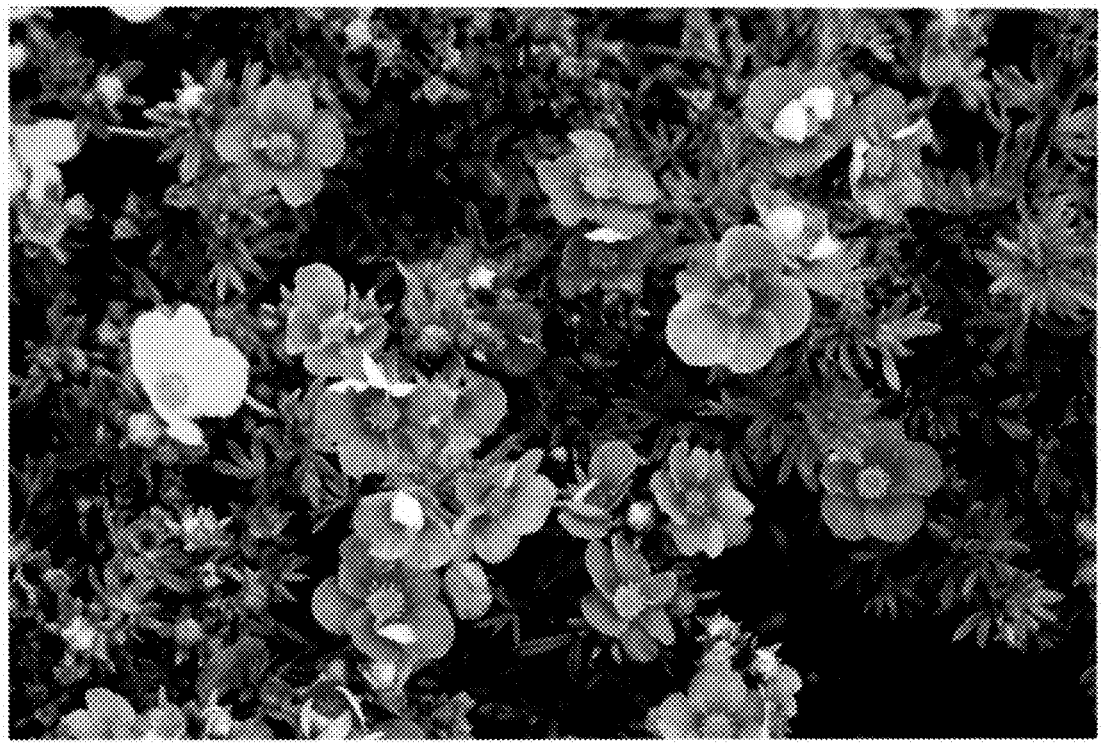

* * * * *